US006923176B2

(12) United States Patent
Ranzinger

(10) Patent No.: US 6,923,176 B2
(45) Date of Patent: Aug. 2, 2005

(54) RESUSCITATION TUBE

(75) Inventor: Gisbert Ranzinger, Aichwald (DE)

(73) Assignee: Willy Rusch GmbH (DE)

( * ) Notice: Subject to any disclaimer, the term of this patent is extended or adjusted under 35 U.S.C. 154(b) by 454 days.

(21) Appl. No.: 10/108,003

(22) Filed: Mar. 26, 2002

(65) Prior Publication Data

US 2003/0183234 A1 Oct. 2, 2003

(51) Int. Cl.[7] ............................................. A61M 16/00
(52) U.S. Cl. ........................... 128/200.26; 128/207.14; 128/207.15; 604/96.01
(58) Field of Search ..................... 128/207.14, 207.15, 128/207.16, 207.18, 842, 200.26; 604/19, 96.01, 98.01, 99.01

(56) References Cited

U.S. PATENT DOCUMENTS

| | | | |
|---|---|---|---|
| 2,862,498 A | | 12/1958 | Weekes |
| 4,090,518 A | | 5/1978 | Elam |
| 4,231,365 A | | 11/1980 | Scarberry |
| 4,688,568 A | | 8/1987 | Frass et al. |
| 5,065,755 A | * | 11/1991 | Klafta ................... 128/200.26 |
| 5,499,625 A | | 3/1996 | Frass et al. |
| 5,873,362 A | | 2/1999 | Parker |
| 6,443,156 B1 | * | 9/2002 | Niklason et al. ....... 128/207.14 |

FOREIGN PATENT DOCUMENTS

| | | | |
|---|---|---|---|
| AT | 384 738 B | 12/1987 | |
| AT | 384738 | 12/1987 | .......... A61M/16/00 |
| DE | 21 20 164 A | 11/1972 | |
| EP | 0 092 618 A | 11/1983 | |
| EP | 0 747 077 A | 12/1996 | |
| GB | 2 168 256 A | 6/1986 | |

* cited by examiner

Primary Examiner—Henry Bennett
Assistant Examiner—Camtu Nguyen
(74) Attorney, Agent, or Firm—Walter A. Hackler

(57) ABSTRACT

In a resuscitation tube (1) comprising a tube wall for alternative artificial endotracheal or esophageal obturator respiration, with a first lumen (2) and a second lumen (3) extending substantially parallel thereto, wherein a first inflatable balloon (5) surrounding the tube wall is disposed in the region of the end of the resuscitation tube (1) facing the body, and a second inflatable balloon (8) surrounding the tube wall (22) is disposed at a separation from the first inflatable balloon (5), an axial opening (10) of the first lumen (2) is disposed directly at the end of the second balloon (8) facing the body, and the resuscitation tube (1) is formed with one lumen in the region of the first balloon (5). This permits insertion of intubation aids via the first lumen (2) such that the resuscitation tube can be used with versatility.

9 Claims, 1 Drawing Sheet

RESUSCITATION TUBE

BACKGROUND OF THE INVENTION

1. Prior Art

The invention concerns a resuscitation tube comprising a tube wall for alternative artificial endotracheal or esophageal obturator respiration with a first lumen and a second lumen extending substantially parallel thereto, wherein a first inflatable balloon, which surrounds the tube wall, is disposed in the region of the end of the resuscitation tube facing the body, and, at a separation therefrom, a second inflatable balloon is disposed which surrounds the tube wall.

A resuscitation tube of this type has been disclosed e.g. in AT 384 738.

Known resuscitation tubes often have two lumina. At the same time, one of the lumina is open at both ends. The other lumen is closed at its end facing the body. Respiration through this lumen is ensured in that the tube wall has lateral air inlets communicating with this lumen. This lumen is suited exclusively for respiration and cannot be used for anything else.

AT 384 738 discloses a resuscitation tube for esophageal obturator or alternatively artificial endotracheal or esophageal obturator respiration which has an inflatable balloon collar in the region of the tube tip and air outlet openings in the tube wall in the pharyngeal region. To provide reliable use of the tube in particular in emergency situations, a balloon surrounding the tube wall is provided above the air outlet openings, which has substantially the shape of a torus when inflated.

2. Object of the Invention

In contrast thereto, it is the object of the present invention to provide a resuscitation tube, which can be used with improved versatility.

SUBJECT MATTER OF THE INVENTION

In accordance with the invention, this object is achieved in that an axial opening of the first lumen is disposed directly at the end of the second balloon (oropharyngeal balloon) facing the body and that the resuscitation tube is formed with one lumen in the region of the first balloon.

Thereby, the tube has a shorter first lumen and a longer second lumen. In contrast to prior art, the first lumen is not closed at the end facing the body but has an axial opening there. The first lumen can therefore be used for artificial respiration as well as for guidance (for medical instruments). For example, a bronchoscope, a tracheal tube or other intubation aids can be applied through the first lumen. The bronchoscope can be used for inspection of the trachea and suction of tracheal secretions. Additionally, a guiding catheter can be introduced via which or along which the resuscitation tube can be inserted. The first balloon seals optionally within the esophagus or within the trachea whereas the second balloon always seals within the pharyngeal space. When the resuscitation tube has been inserted, the opening of the first lumen is in the region of the inlet of the larynx. The first lumen can have additional lateral air inlets in the tube wall in the region between the first and second balloon for improved respiration. For further applications, optionally further lumina can be provided on the tube. A further lumen can be formed in the wall of the resuscitation tube, which extends to the tip (terminal end) of the resuscitation tube and is open there. This lumen can be guided out of the wall of the resuscitation tube in the section of the resuscitation tube facing away from the body and verge into a separate line (gas discharge line) which can be connected to suitable test equipment (capnography). This separate line permits withdrawal of small gas volumes from the tip region of the positioned resuscitation tube and analysis by suitable detection devices (e.g. $CO_2$ portion in the detected gas volume). The position of the tip of the resuscitation tube can be determined via such determination of the gas composition in the analyzed gas volume. It is understood that the resuscitation tube can be provided with connectors for connecting to artificial respiration aids.

The end of the first lumen facing the body is preferably disposed directly at the end of the second balloon facing the body. This measure ensures on the one hand that the first lumen does not block the entry to the trachea if the second lumen has been pushed a little too far into the esophagus, and an easy introduction of an intubation aid into the trachea. On the other hand, the opening of the first lumen and the associated cross-sectional enlargement of the tube do not represent an enlarged obstacle when introducing the tube. Irritation of tissue is thereby minimized. The tube can have a smaller diameter in the end section of the region (tip) facing the body if the tube is formed with one lumen in the region of the first balloon. This facilitates introduction of the resuscitation tube and increases the comfort for the patient. If the opening of the first lumen is disposed in the direct vicinity of the second balloon, inadvertent introduction of both lumina into the esophagus is not possible which could impede artificial respiration.

In a particularly preferred embodiment, the region of the opening of the first lumen is provided with at least one spacer which prevents abutting of the epiglottis on the opening and resulting obstruction of the airways.

A further development is characterized in that the spacer is formed as at least one bar overlapping the opening whose one end is fastened to the shaft of the second lumen and whose other end is mounted to the outer side of the opening of the first lumen. One or more bars can prevent the epiglottis from closing the opening and still leave at least one opening free through which artificial respiration is possible. The at least one bar is disposed preferably dorsocaudally such that the at least one bar can support introduction of a tracheal tube, which has optionally been introduced through the first lumen, in the direction of the inlet of the larynx.

In an alternative embodiment, the spacer is formed as a tongue, in particular an elastic tongue, mounted to the outside of the opening of the first lumen, wherein the free end of the tongue is disposed in the shaft region of the second lumen, in particular abuts on the outer surface of the shaft. When introducing a tracheal tube or another intubation aid, the free end of the tongue is pressed or spread away from the shaft of the second lumen to free an opening. When the tongue abuts on the shaft, it leaves enough free space for easy flow of respiratory air. At the same time, it prevents, similar to the at least one bar, that the first lumen is blocked by food remains or anatomical structures (soft parts). The basis of the tongue is preferably mounted or hinged to the outer side of the opening of the first lumen. The tongue advantageously tapers towards the free end.

In an embodiment of the invention, the shaft of the second lumen has an elevation in the opening region of the first lumen, with the elevation facing the opening. This elevation can prevent undesired obstruction of the opening. In particular, it can be formed such that it directs an introduced intubation aid in the direction of the larynx.

In a preferred embodiment of the invention, the resuscitation tube tapers beyond the first balloon towards the free end of the resuscitation tube. This measure provides the tube tip with atraumatic properties. The resuscitation tube can therefore be introduced without any danger of injuring the larynx, the trachea or the esophagus.

The resuscitation tube preferably comprises a tube tip which is formed like the tip of a fountain pen.

In a further embodiment, the resuscitation tube has, basically, an oval, preferably transversely oval cross-section at least on the side of the second balloon facing away from the body. A tube of this design compensates for too narrow a distance between the incisor edges which often limits intubation.

If the inflated second balloon has, basically, a transversely oval cross-sectional shape, the balloon can be adjusted in an optimum manner to the anatomy of the patient by reducing the pressure onto the neighboring tissue of the oropharynx. In particular, a balloon of such design permits central positioning in the oropharynx. The designated balloon material is material without natural latex, in particular synthetic latex.

Further features and advantages of the invention can be extracted from the following description of an embodiment of the invention, the figures of the drawings which show details which are essential to the invention, and from the claims. The individual features can be realized in a variant of the invention either individually or collectively in any arbitrary combination.

DRAWING

An embodiment of the inventive resuscitation tube is shown in the schematic drawing and is explained in the following description.

DESCRIPTION OF THE EMBODIMENT

Figure 1:
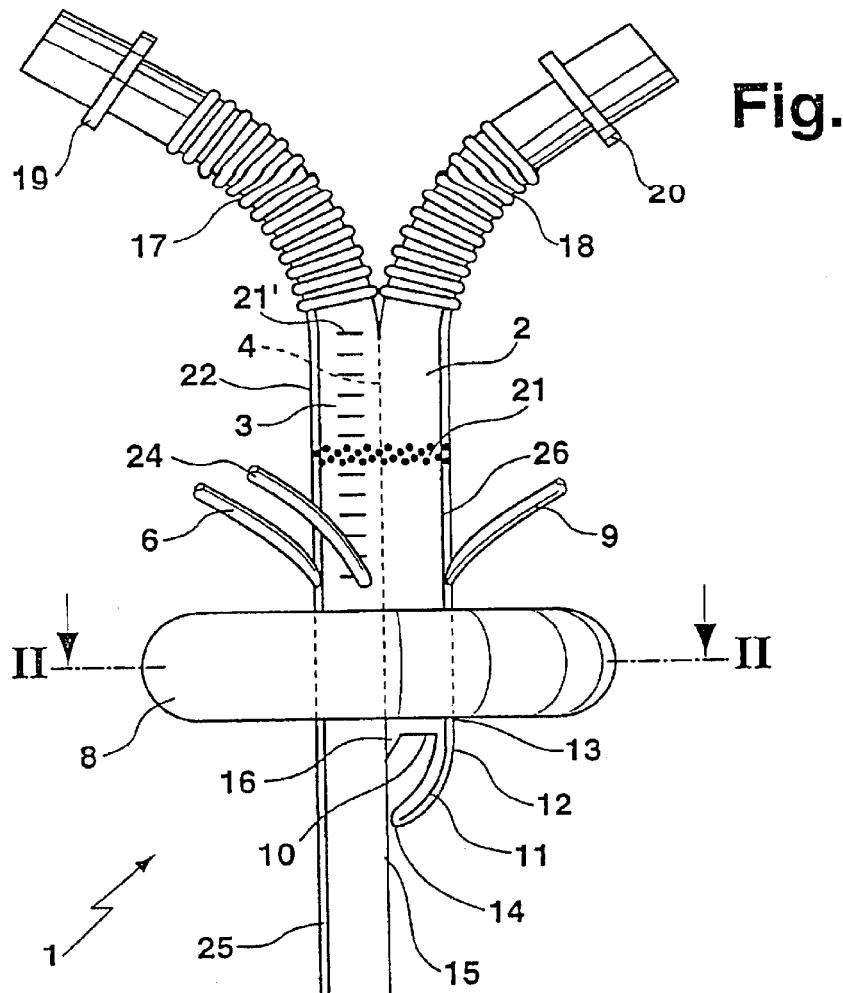
FIG. 1 shows a top view onto a resuscitation tube.

The figures are highly schematic to emphasize the essential inventive features. The dimensions in the drawings are only exemplary and are not to be taken to scale.

FIG. 1 shows a resuscitation tube 1 comprising a first and a second lumen 2, 3 which are separated from each other by a dividing wall 4 in the region of the resuscitation tube 1 facing away from the body. Contrary to the region facing the body, the resuscitation tube 1 is formed with two lumina in the region facing away from the body, wherein the second lumen 3 has an open end at the end of the resuscitation tube 1 facing the body. The end region is formed with an inflatable first balloon 5. For inflating the first balloon 5, a feed line 6 is provided which is guided along the resuscitation tube 1 to the first balloon 5.

After the first balloon 5, the tube tip 7 tapers towards the open terminal end of the resuscitation tube 1 facing the body, thereby having atraumatic properties. The second lumen 3 is slightly curved out of the plane of the drawing in the region facing the body. At a separation from the first balloon 5, a second inflatable balloon 8 is provided which surrounds the first and second lumina 2, 3. A feed line 9 is provided for inflating the second balloon 8. Both feed lines 6, 9 terminate in an interface (not shown) for a Luer connector. The first lumen 2 terminates directly at the end of the second balloon 8 facing the body and has an axial opening 10 there. The opening region is provided with a spacer 11 formed as a tongue whose base 12 at the one end is elastically mounted to the outer side 13 of the opening 10. The free end 14 of the spacer 11 is shown at a slight separation from the shaft 15 of the second lumen 3 in FIG. 1, however, it can abut on the shaft 15, too. Moreover, an elevation 16 is provided on the shaft 15 in the opening region which can guide an intubation aid to be inserted into the first lumen 2 or a bronchoscope. At the end facing away from the body, the lumina 2, 3 comprise deviation legs 17, 18 which are preferably buckling-resistant ribbed hoses. In order to be able to connect to respiratory aids, 15 mm connectors 19, 20 are provided. A marking 21 shows the degree of possible insertion of the resuscitation tube 1. The intubation depth can be read off via a graduation 21' or scale. The separations between the graduation markings are 1 cm. A third lumen for the capnography is provided in the wall 22 of the resuscitation tube 1 whose one end terminates in an opening 23 and the other end verges into a gas discharge line 24 which terminates in a Luer interface (not shown). The outer circumference of the resuscitation tube 1 is provided with markings 25, 26 impermeable to X-rays through which the position of the placed resuscitation tube 1 can be controlled. The marking 25 extends along the second lumen 3 and the marking 26 extends along the first lumen 2. The marking 26 continues along the spacer 11 in the embodiment described.

Figure 2:
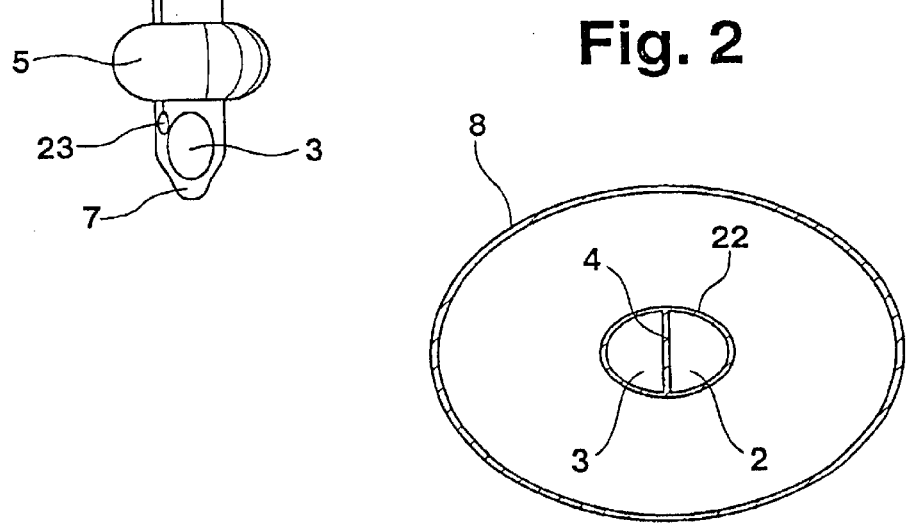
FIG. 2 shows a sectional view in accordance with line II—II of FIG. 1

FIG. 2 shows a cross-section according to line II—II of FIG. 1. In the region facing away from the body in which they extend substantially parallel, the first and second lumen 2, 3 are separated from each other by a dividing wall 4. Towards the outside they are delimited by the tube wall 22. The cross-sectional shape of the resuscitation tube 1 is preferably transversely oval in this region. The tube wall 22 is surrounded by the second balloon 8 which also assumes a preferably transverse oval shape when inflated.

Depending on the application of the resuscitation tube 1, the end of the resuscitation tube 1 facing the body is introduced into the trachea or esophagus. Subsequently, the first balloon 5 is inflated. If the resuscitation tube 1 is located in the trachea, respiration is effected via the second lumen 3. If the resuscitation tube 1 is placed in the esophagus, respiration is effected via the first lumen 2. The pharyngeal space is sealed by inflating the second balloon 8. In the inflated state of the second balloon 8, the resuscitation tube 1 is stabilized in its placed position and centered. A bronchoscope can e.g. be inserted into the trachea via the first lumen 2, thereby spreading the spacer 11 away from the shaft 15. At the same time, a stomach tube can be introduced via the second lumen 3 if required.

In a resuscitation tube 1 comprising a tube wall 22 for alternative artificial endotracheal or esophageal obturator respiration with a first lumen 2 and a second lumen 3 extending substantially parallel thereto, wherein a first inflatable balloon 5 surrounding the tube wall 22 is disposed in the region of the end of the resuscitation tube 1 facing the body, and a second inflatable balloon 8 surrounding the tube wall 22 is disposed at a separation from the first inflatable balloon 5, an axial opening 10 of the first lumen 2 is disposed directly at the end of the second balloon 8 facing the body, and the resuscitation tube 1 is formed with one lumen in the region of the first balloon 5. This permits insertion of intubation aids via the first lumen 2 such that the resuscitation tube can be used with versatility.

I claim:

1. Resuscitation tube (1) comprising a tube wall (22) for alternative artificial endotracheal or esophageal respiration, with a first lumen (2) and a second lumen (3) extending substantially parallel thereto, wherein a first inflatable balloon (5) surrounding the tube wall (22) is disposed in the region of the end of the resuscitation tube (1) facing the body, and a second inflatable balloon (8) surrounding the tube wall (22) is disposed at a separation from the first inflatable balloon (5), an axial opening (10) of the first lumen (2) is disposed directly at the end of the second balloon (8) facing the body and that the resuscitation tube (1) is formed with one lumen in the region of the first balloon and at least one spacer (11) is provided in a region of the opening (10) of the first lumen (2), the spacer (11) being a tongue or bar mounted to an outer side of the opening (10) of the first lumen (2) and preventing abutment of the epiglottis to the opening (10) of the first lumen (2).

2. Resuscitation tube according to claim 1, wherein the at least one spacer (11) is is formed as a bar overlapping the opening (10) and is additionally mounted to a shaft of a second lumen (3).

3. Resuscitation tube according to claim 2, wherein the spacer (11) is formed as a tongue having a free end supporting on an outer surface of a shaft of a second lumen.

4. Resuscitation tube according to claim 2, characterized in that the spacer (11) is formed as a tongue, in particular an elastic tongue, which is mounted to the outside (13) of the opening (10) of the first lumen (2), wherein the free end (14) of the tongue is disposed in the shaft region of the second lumen (3), in particular is supported on the outer surface of the shaft (15).

5. Resuscitation tube according to any one of the preceding claims, characterized in that the shaft (15) of the second lumen (3) has an elevation (16) in the opening region of the first lumen (2), with the elevation (16) facing the opening (10).

6. Resuscitation tube according to any one of the preceding claims, characterized in that the resuscitation tube (1) tapers beyond the first balloon (5) to the free end of the resuscitation tube (1).

7. Resuscitation tube according to any one of the preceding claims, characterized in that the resuscitation tube (1) has a tube tip (7) which is formed like the tip of a fountain pen.

8. Resuscitation tube according to any one of the preceding claims, characterized in that the resuscitation tube (1) has a basically oval, in particular transversely oval cross-section, at least on the side of the second balloon (8) facing away from the body.

9. Resuscitation tube according to any one of the preceding claims, characterized in that the second balloon (8) has a basically transversely oval cross-section when inflated.

* * * * *